(12) United States Patent
Vogelsang

(10) Patent No.: US 9,650,598 B2
(45) Date of Patent: May 16, 2017

(54) INTRODUCING SCREW FOR BIOGAS PLANTS

(71) Applicant: HUGO VOGELSANG MASCHINENBAU GMBH, Essen (DE)

(72) Inventor: Hugo Vogelsang, Essen (DE)

(73) Assignee: Hugo Vogelsang Maschinenbau GmbH, Essen (DE)

( * ) Notice: Subject to any disclaimer, the term of this patent is extended or adjusted under 35 U.S.C. 154(b) by 159 days.

(21) Appl. No.: 14/356,707

(22) PCT Filed: Nov. 9, 2012

(86) PCT No.: PCT/EP2012/072313
§ 371 (c)(1),
(2) Date: Aug. 7, 2014

(87) PCT Pub. No.: WO2013/068555
PCT Pub. Date: May 16, 2013

(65) Prior Publication Data
US 2014/0339054 A1 Nov. 20, 2014

(30) Foreign Application Priority Data
Nov. 11, 2011 (DE) .................... 20 2011 107 750 U

(51) Int. Cl.
*B65G 33/14* (2006.01)
*C12M 1/26* (2006.01)
(Continued)

(52) U.S. Cl.
CPC ............. *C12M 33/16* (2013.01); *B65G 33/14* (2013.01); *B65G 33/22* (2013.01); *C12M 21/04* (2013.01);
(Continued)

(58) Field of Classification Search
CPC B65G 33/14; B65G 33/22; B65G 2812/0527; B65G 2812/0538; C12M 21/04; C12M 33/16; Y02E 50/343
(Continued)

(56) References Cited

U.S. PATENT DOCUMENTS 1,423,698 A * 7/1922 Thurston ................ B65G 65/46
198/535
3,508,683 A * 4/1970 Van Der Schee ...... B65G 33/00
198/661
(Continued)

FOREIGN PATENT DOCUMENTS

CN 2460496 Y 11/2001
CN 1413245 A 4/2003
(Continued)

OTHER PUBLICATIONS

Chinese Patent Application No. 201280055043.9, Office Action (and English translation) dated Nov. 15, 2014.
(Continued)

*Primary Examiner* — Gerald McClain
*Assistant Examiner* — Keith R Campbell
(74) *Attorney, Agent, or Firm* — Kilpatrick Townsend & Stockton LLP; Dean W. Russell

(57) ABSTRACT

A screw conveyor for introducing organic matter into a biogas digester that is under internal gas pressure. A biogas plant may be provided with such a screw conveyor, and methods for feeding organic solids to such a biogas plant may be performed. A plug section of the screw conveyor has an expansion region in which the passage cross-section between the conveying screw and the screw pipe widens in the conveying direction and a constriction region located downstream from the expansion region, in which the pas-
(Continued)

sage cross-section between the conveying screw and the screw pipe is reduced in the conveying direction.

12 Claims, 6 Drawing Sheets

(51) Int. Cl.
    *B65G 33/22*     (2006.01)
    *C12M 1/107*     (2006.01)

(52) U.S. Cl.
    CPC ..... *B65G 2812/0538* (2013.01); *Y02E 50/343* (2013.01)

(58) Field of Classification Search
    USPC .......................................................... 198/670
    See application file for complete search history.

(56) References Cited

U.S. PATENT DOCUMENTS

| | | | | |
|---|---|---|---|---|
| 3,602,552 | A * | 8/1971 | Morgan | F04D 3/02 198/672 |
| 4,838,995 | A * | 6/1989 | Klausen | B30B 9/12 162/18 |
| 5,009,795 | A * | 4/1991 | Eichler | A23J 3/346 100/117 |
| 5,732,618 | A * | 3/1998 | Buehl | B30B 9/127 100/112 |
| 6,145,766 | A * | 11/2000 | Mraz | B30B 9/121 241/260.1 |
| 6,251,643 | B1 * | 6/2001 | Hansen | C12M 21/04 426/447 |
| 6,258,262 | B1 * | 7/2001 | Katabe | B01D 29/23 100/116 |
| 6,588,331 | B2 * | 7/2003 | Thibodeau | B30B 9/12 100/110 |
| 6,736,054 | B2 * | 5/2004 | Dionne | B30B 9/121 100/110 |
| 6,945,487 | B1 * | 9/2005 | Obitz | D21D 1/20 241/260.1 |
| 7,357,074 | B2 * | 4/2008 | Kraft | B30B 9/121 100/117 |
| 8,181,570 | B2 * | 5/2012 | Svedberg | B30B 9/122 100/117 |
| 9,193,530 | B2 * | 11/2015 | Trudslev | B65G 65/46 |
| 2009/0022570 | A1 * | 1/2009 | Craig | C10J 3/30 414/197 |
| 2010/0317053 | A1 * | 12/2010 | Stromberg | B01F 7/00766 435/41 |

FOREIGN PATENT DOCUMENTS

| | | |
|---|---|---|
| CN | 101549790 A | 10/2009 |
| DE | 29903208 U1 | 8/2000 |
| DE | 20216090 U1 | 11/2003 |
| DE | 10252527 A1 | 5/2004 |
| DE | 202009003782 U1 | 6/2009 |
| DE | 202010000550 U1 | 7/2010 |

OTHER PUBLICATIONS

Chinese Patent Application No. 201280055043.9, Office Action (and English translation) dated Jun. 12, 2015.
PCT/EP2012/072313, International Search Report and Written Opinion dated May 13, 2013, 27 pages.

* cited by examiner

INTRODUCING SCREW FOR BIOGAS PLANTS

CROSS REFERENCE TO RELATED APPLICATIONS

This application is the U.S. national phase entry of International Patent Application Serial No. PCT/EP2012/072313, filed Nov. 9, 2012, which application claims priority to German Patent Application No. 202011107750.4, filed Nov. 11, 2011.

FIELD OF THE INVENTION

The invention relates to a screw conveyor for introducing organic matter, such as organic materials and organic solids, into a biogas digester that is under internal gas pressure. The invention further relates to a biogas plant provided with such a screw conveyor, and to a method for feeding organic solids to such a biogas plant.

BACKGROUND

In biogas plants, a combustible gas is produced by digesting organic matter in a digester, typically by methane formation. Such digesters are typically operated under an internal gas pressure which is generated by sealing the digester gas-tightly and by controlled extraction of the biogas produced therein. Digesters may be loaded continuously or semi-continuously (batch-wise) with organic solids in order to keep the digestion process going. Both during loading and also after loading, the pressure inside the digester must be overcome and maintained, and undesired leakage of materials from the digester must be prevented.

An apparatus for introducing livestock waste into a liquid manure digester is known from DE 202 16 090 U1, in which the livestock waste is filled into the digester from above by means of a plurality of screw conveyors. A similar apparatus for loading a digester vessel of a biogas plant is known from DE 299 03 208.

In addition to these prior art apparatuses for loading a digester vessel from above, devices for loading the digester vessel from below are also known which in many cases achieve better mixing of the supplied solid material with the solid material already in the vessel.

A basic problem when feeding solid materials into the digester is that a reverse flow of solids, liquids or gases from the digester through the feed device must be reliably prevented. This prevention of reverse flow must be achieved not only when the feed device is in operation but also when the feed device is not in operation, for example when solid materials are semi-continuously fed in successive feed operations performed at intervals.

A conveying device for introducing organic solids into a digester vessel, said device comprising a screw conveyor having a section with no flighting, is known from DE 102 52 527 B4. The aim of this apparatus is to compress the material being conveyed in the region of the flightless section in order to seal the conveying screw against the reverse flow of solids, liquids and gas. Due to the flightless section in the screw conveyor, the feed rate of the screw conveyor is reduced, however, and in the case of solid materials which are difficult to convey, it is possible that the internal resistance in the screw conveyor increases to such an extent that the feed rate falls to zero, thus resulting in blockage.

A more advanced feeding device for feeding solid material into a digester vessel and which likewise has a flightless section and which is also equipped with an axially movable flighting is known from DE 20 2010 000 550 U1. This axial mobility is aimed at preventing blockages of the screw conveyor. Although the device has proved to be advantageous in this respect, it requires complex and error-prone mounting and driving of the conveying screw in order to achieve the superimposed axial mobility and rotation.

SUMMARY

The object of the invention is to provide a device for feeding organic solids into biogas plants, with which reliable transport of the organic solids is achieved while at the same time ensuring that the biogas vessel is sealed against any escape of solids, liquids or gases through the feeding device when the feeding device is in operation or idle.

This object is achieved, according to the invention, by a screw conveyor of the kind initially specified, in which the plug section has an expansion region in which the passage cross-section between the conveying screw and the screw pipe widens in the conveying direction, and a constriction region located downstream from the expansion region, in which the passage cross-section between the conveying screw and the screw pipe is reduced in the conveying direction.

The screw conveyor device thus defined allows organic solids to be fed efficiently and reliably into a digester that is under pressure, without the risk arising of solids, liquids or gases escaping from the digester through the screw conveyor, whatever the feed arrangement and whatever the operating state. This is achieved by providing a plug section in the screw conveyor, where the organic solids are efficiently compacted in such a way that they form a reliable barrier against such escape of solids, liquids or gases. At the same time, said plug section is designed in such a way, by means of flighting embodied therein, that any stoppage due to blockage can be reliably prevented and that the organic solids are conveyed reliably when the screw conveyor is in operation. The plug section is characterised in that its passage cross-section is initially expanded and subsequently constricted again in the conveying direction, thus achieving the desired compaction and sealing.

The passage cross-section is understood here to be the space that exists as a cross-section inside the screw pipe and which is not filled by any stationary or moving elements installed inside the screw pipe, such as the conveying screw with the flights arranged thereon. In typical screw conveyors, the passage cross-section is therefore embodied as an annular gap which is formed between the screw body and the inner wall of the screw pipe and which is partially reduced, depending on the number of flights, by one or more cross-sections of the flights. This passage cross-section may be widened by reducing the cross-sections of the components inside the screw pipe, for example by reducing the diameter of the screw body or by increasing the inner diameter of the screw pipe, or by implementing both measures. The passage cross-section may be reduced, in contrast, by increasing the cross-sections of the components installed inside the screw pipe, for example by increasing the diameter of the screw body or by thickening the cross-section of the flighting, and alternatively or additionally by reducing the inner diameter of the screw pipe.

In order to achieve efficacious compaction in accordance with the invention, the passage cross-section is initially expanded in the upstream region of the plug section, viewed in the conveying direction. The passage cross-section is then reduced in the downstream section that follows in the conveying direction, that is to say in the largest part of the plug section in the axial direction, which comprises the middle and the end region of the plug section. It should be understood as a basic principle that both the expansion and also the reduction of the passage cross-section may be carried out in one or more steps, that is say discontinuously, and that, alternatively or in combination therewith, said expansion and reduction may also be carried out entirely continuously or continuously in sections. A continuous change in a passage cross-section should be understood here to mean, for example, a constantly increasing or constantly decreasing change in cross-section, although it may also mean a progressive or diminishing reduction in cross-section.

According to a first preferred embodiment, the conveying screw has a first passage cross-section between the conveying screw and the screw pipe in a region immediately at the beginning of the plug section in the conveying direction, a second passage cross-section, which is enlarged relative to that of the first passage cross-section, in the initial region of the plug section, and at the end of the plug section, a third passage cross-section reduced in relation to the second. This configuration defines an initial widening of the passage cross-section over a short axial extension, followed by a reduction in the passage cross-section over a longer axial section of the plug section, which has proved to be particularly advantageous with regard to efficient compaction and safe conveying.

It is further preferred that the passage cross-section in the plug section is expanded in steps in the conveying direction in the initial region and/or is continuously reduced over most of the plug section. As thus defined, this expansion in steps, followed by a continuous reduction in passage cross-section, reliably prevents any blockage of the screw conveyor, while at the same time achieving sufficient compaction of the solids in the plug section, in order to provide an adequate seal against the escape of gas.

According to another preferred embodiment, the passage cross-section changes before the plug section, starting from a first passage cross-section having a cross-sectional geometry characterised by a first ball passage, to a second passage cross-section having a cross-sectional geometry characterised by a second ball passage that is larger than the first ball passage, and changes further to a third passage cross-section having a cross-sectional geometry characterised by a third ball passage which is smaller than the second ball passage, wherein the first and the third ball passages are preferably congruent. A ball passage should be understood here to mean the maximum diameter that a ball may have in order to be conveyed in the screw conveyor through a respective place characterised by the ball passage. The ball passage is specifically relevant when applied to the conveying of organic solids in biogas plants, therefore, because it allows the screw conveyor to be characterised in terms of its capacity to convey the hard materials contained in organic solids, such as stones, without being damaged or blocked as a result. The greater the ball passage, the less delicate and the more efficient the screw conveyor is with regard to this characteristic. What this embodiment of the invention achieves, in particular, is that the organic solids are compacted by appropriate reductions in the passage cross-section, without the ball passage, starting from an initial ball passage, necessarily having to decrease to an amount less than said initial ball passage anywhere along the entire length of the screw conveyor.

According to another advantageous aspect of the invention, a screw conveyor of the kind initially described is provided which is characterised by a separation section disposed upstream from the plug section, comprising a plurality of openings in the screw pipe and a fluid collection apparatus outside the screw pipe. The screw conveyor can specifically be embodied according to any one of the inventive embodiments described in the foregoing. The separation section provided in accordance with this variant of the invention prevents the content of the screw conveyor from being enriched with liquid and thus from acquiring too low a viscosity to still be conveyed efficiently in the screw conveyor. Dewatering is effected here by a plurality of openings distributed around the circumference along the axial extension of the separation section, for example by embodying the screw pipe like a sieve in the region of the separation section. Disposing the separation section upstream from the plug section provides additional support for efficient compaction of the organic solids in the plug section.

Another aspect of the invention relates to a screw conveyor of the kind initially described, which is characterised by a flushing fluid port for feeding a flushing fluid into the passage cross-section between the screw pipe and the conveying screw in the region of the second screw pipe end downstream from the plug section. Such a flushing port allows the compacted organic mass, with reduced liquid content where relevant, to be conveyed reliably out of the screw conveyor in the region of the outlet opening at the second screw pipe end, namely by additionally diluting said mass, i.e. by reducing its viscosity. A carrier medium such as recirculate or liquid manure, more particularly a fluid extracted in the region of a separation section, can be used here for flushing purposes. Flushing in the fluid also promotes the mixing process within the compacted, previously produced plug, thus providing a favourable starting point for later digestion.

It is particularly preferred in this regard that a flushing port is arranged at the end face of the screw pipe and opens into a flushing line extending axially in the longitudinal direction of the screw pipe, said flushing line extending from the second end of the screw pipe to at least one radial flushing fluid port that opens into the passage cross-section between the conveying screw and the screw pipe. This variant provides an advantageous construction for introducing the flushing fluid in the region of the second end of the screw conveyor, and which allows, more particularly in cooperation with a radial outlet opening from the screw pipe, a maintenance-friendly as well as robust construction. It is advantageous when a plurality of flushing fluid ports is provided which are radially distributed over the circumference and extend from the interior of the screw pipe or flushing line so that the organic solids are reliably mixed with the flushing fluid in the region of the second end.

According to another development of the invention in this regard, the conveying screw is embodied in the region of the second end as a hollow shaft for conducting the flushing fluid inside the conveying screw. This variant allows the flushing fluid to be supplied directly with efficient mixing into the region of the organic solids.

It is still further preferred that the conveying screw is rotatably mounted in the region of the second end on a pipe connection which is fixed torque-resistantly to the screw pipe and which extends axially into a hollow space in the conveying screw. This embodiment achieves efficient flushing and mixing in the region of the second end, while also allowing the conveying screw to be mounted simply and robustly as far as assembly and installation is concerned. The pipe connection can be used, more particularly, to conduct the flushing fluid.

According to another preferred embodiment of the invention, the screw conveyor of the kind initially described can be developed by providing at least one flight which is disposed in the region of the second screw pipe end and which is detachably fixed to the conveying screw. In the region of the second end, flights can basically be arranged helically around the screw shaft or may extend axially like paddles on the screw shaft in the longitudinal direction. Both variants of flighting may be used specifically to convey the organic solids, which may be diluted with a flushing fluid, out of a radially disposed outlet opening in the screw pipe. These flights in the region of the second end can be used as design parameters, in particular, in that they reduce the passage cross-section at said second end to a greater or lesser extent on account of their geometry. For example, when conveying organic solids with a high fluid content, it can be advantageous to mount flights in the region of the second end that bring about a large reduction in cross-section in said end section, in order to support compaction in the plug section as a result. Conversely, when conveying organic solids that are particularly dry, as small a reduction in cross-section as possible is desirable in the region of the second end, so suitably small flights can be mounted. In order to adapt the screw conveyor device according to the invention in a simple way to different consistencies of organic solids, and to achieve ideal compaction and conveying in all cases, it is therefore advantageous when the flights in the region of the second end are detachably mounted. It should be understood in this regard that these flights in the region of the second end may be embodied as an extension of the flights on the screw shaft itself and may accordingly be designed as a detachably mounted section, or the flights may be embodied as separate components, possibly with different flight pitches from the flight(s) in the rest of the conveying screw. A single flight or plurality of flights can basically be arranged in the region of the second end and, in the case of a plurality of flights, one or more thereof may be mounted detachably.

It is further preferred that the a screw conveyor according to the invention is developed by a first flight which can be mounted on the screw conveyor and by a second flight which can be mounted alternatively to the first and which has a cross-section that fills out a larger cross-sectional area, relative to the first flight, of the passage cross-section between the conveying screw and the screw pipe. This variant provides a set of different flights for the region at the second end of the screw conveyor, thus allowing adaptation to different organic solids or conveying tasks.

Another aspect of the invention relates to a screw conveyor constructed as initially described and which is developed in such a way that the inner wall of the screw pipe encloses a non-circular inner cross-sectional area. This variant of the invention solves a specific problem of screw conveyors operated with different solids and which consists in the conveying capability of such screw conveyors being compromised when the organic solids have particular consistencies, due to some of the conveying material rotating inside the conveyor pipe. As soon as all or some of the conveyed material rotates along with the conveying screw, the feed rate is significantly reduced or may even fall to zero. Giving the inner cross-sectional area enclosed by the inner wall of the screw pipe a non-circular shape reliably prevents the conveyed material from rotating with the screw conveyor, in that the conveyed material can rest against areas of the pipe wall having a non-circular geometry, thus increasing adhesion to the pipe. A non-circular inner cross-sectional area should be understood in this regard to be any cross-sectional area which is not defined by a circle, which specifically includes oval cross-sections and irregularly shaped cross-sections, for example with a geometry comprising triple or quadruple ellipses.

It is particularly preferred that the inner wall of the screw pipe encloses a polygonal inner cross-sectional area. Such polygonal inner cross-sectional areas may be defined on the outside by a triangular profile, for example, but boundaries defined by rectangular, pentagonal and hexagonal outer profiles are also advantageous in certain applications, and outer profile boundaries defined by polygonal shapes with more than six corners may also be advantageous. It should be understood in this regard that the chosen degree of deviation from a circular cross-section is an important criterion for increasing the adhesion of the solids to the inner wall of the pipe, and is also an important criterion for the size of the gap that occurs between the flighting and the screw pipe, which can result in leakage. The closer the cross-sectional geometry approximates to a circular shape, the smaller the chosen gap size can be, but the less the additional adhesion resulting from non-circular geometry and hence the greater the risk of the solids rotating along with the conveying screw.

According to another aspect of the invention, a screw conveyor is provided which comprises a screw pipe extending in a longitudinal direction and having an inlet opening and an outlet opening in the region of a second screw pipe end, a conveying screw extending in the longitudinal direction and arranged inside the screw pipe and which is rotatably mounted and can be made to rotate by means of a screw conveyor drive, said screw conveyor being characterised characterised in that the inlet opening is designed as a radial opening in the screw pipe and extends across an inlet opening section in the longitudinal direction of the screw pipe, and that in the region of the inlet opening section the conveying screw has a first flighting pitch and a second flighting pitch differing from the first flighting pitch. This screw conveyor may be specifically configured according to the features of the previously described embodiments of the screw conveyor according to the invention. This embodiment of the screw conveyor defines a specific solution to a problem which can arise where solids are fed via an open screw trough forming a radial inlet opening. In such cases of radial feeding over a defined axial region, it is often observed that certain solids can be received unevenly from the screw trough or from the inlet opening, which results in initial reception at the inlet region at the end of the screw conveyor, such that material from those regions of the screw trough lying in the direction of the second end of the screw conveyor are not received until the one end of the screw trough has been emptied. This observed movement of the filling point from the back to the front may cause problems in the case of upstream loading units, such as a push floor, for example, and in particular can make control and regulation processes aimed at qualitative or quantitative control or regulation of the conveying rate much more complicated. This problem also raises the risk of sections of the screw trough becoming overfilled and overflowing, or not being sufficiently filled, which could result in an empty conveyor. A conveyor running empty can specifically result in inadequate seals, which it is the aim of the invention to prevent.

By embodying the inlet opening region of the screw conveyor in accordance with the invention, this uneven reception of the solids from the screw trough is prevented by a specific configuration of the flights. According to the invention, the flighting pitch is adapted to the different filling and reception conditions, with areas where reception from the screw trough is not efficient being provided with a higher flighting pitch than areas which are preferentially filled from the screw trough, which accordingly have a smaller pitch.

More particularly, the flighting pitch may continuously change in the region of the inlet opening section. Such continuous change in flighting pitch can ensure that conveying is safe from blockages and can efficiently counteract any continuous change in the efficiency of reception along the feed hopper.

It is still further preferred that the flighting pitch is shorter in the region of the inlet opening section facing the first screw pipe end than in the region of the inlet opening section facing the second screw pipe end. This embodiment efficiently counteracts the frequently observed problem of material being received from the screw trough to a greater extent in the area near the first end.

Another aspect of the invention relates to a biogas plant comprising a digester which is sealed gas-tightly and which includes a solid matter feed opening in a gas discharge port, said biogas plant according to the invention being characterised by a screw conveyor according to any one of the preceding claims, the outlet opening of which is connected directly to the solid matter feed opening or to a pipeline that is under internal digester pressure and which leads to the solid matter feed opening of the digester. Such a biogas plant provided in accordance with the invention allows reliable, continuous or semi-continuous conveying of organic solids into a digester, while also providing secure sealing against undesired escape of solids, liquids or gases from the screw conveyor when the screw conveyor is in operation or not in operation.

The screw conveyor according to the invention preferably operates according to a method for feeding organic solids into a digester that is under internal pressure, said method comprising the steps of: conveying the organic matter by means of a screw conveyor from an inlet opening to an outlet opening which is connected directly and gas-tightly to the digester, compacting the organic matter in the screw conveyor to prevent or reduce the passage of gas through the screw conveyor, wherein the organic matter are preferably compacted by reducing the passage cross-section of the screw conveyor in the conveying direction and the passage cross-section is further preferably expanded in the conveying direction prior to said reduction, optionally separating fluid from the organic matter by means of a plurality of radial openings in the screw conveyor prior to compacting, and optionally flushing in a fluid after compacting.

The screw conveyor according to the invention can also operate according to a method for conveying solid materials, said method comprising the steps of: conveying the organic matter by means of a screw conveyor from a radial inlet opening extending across an axial section, and further characterised in that the organic solids are conveyed in a first region of the inlet opening by means of a flight having a first pitch and in a second region of the inlet opening downstream from the first region by means of a flight having a second pitch that it is longer than the first pitch.

BRIEF DESCRIPTION OF THE DRAWINGS

A preferred embodiment of the invention shall now be described with reference to the attached Figures, in which.

DETAILED DESCRIPTION

Figure 1:
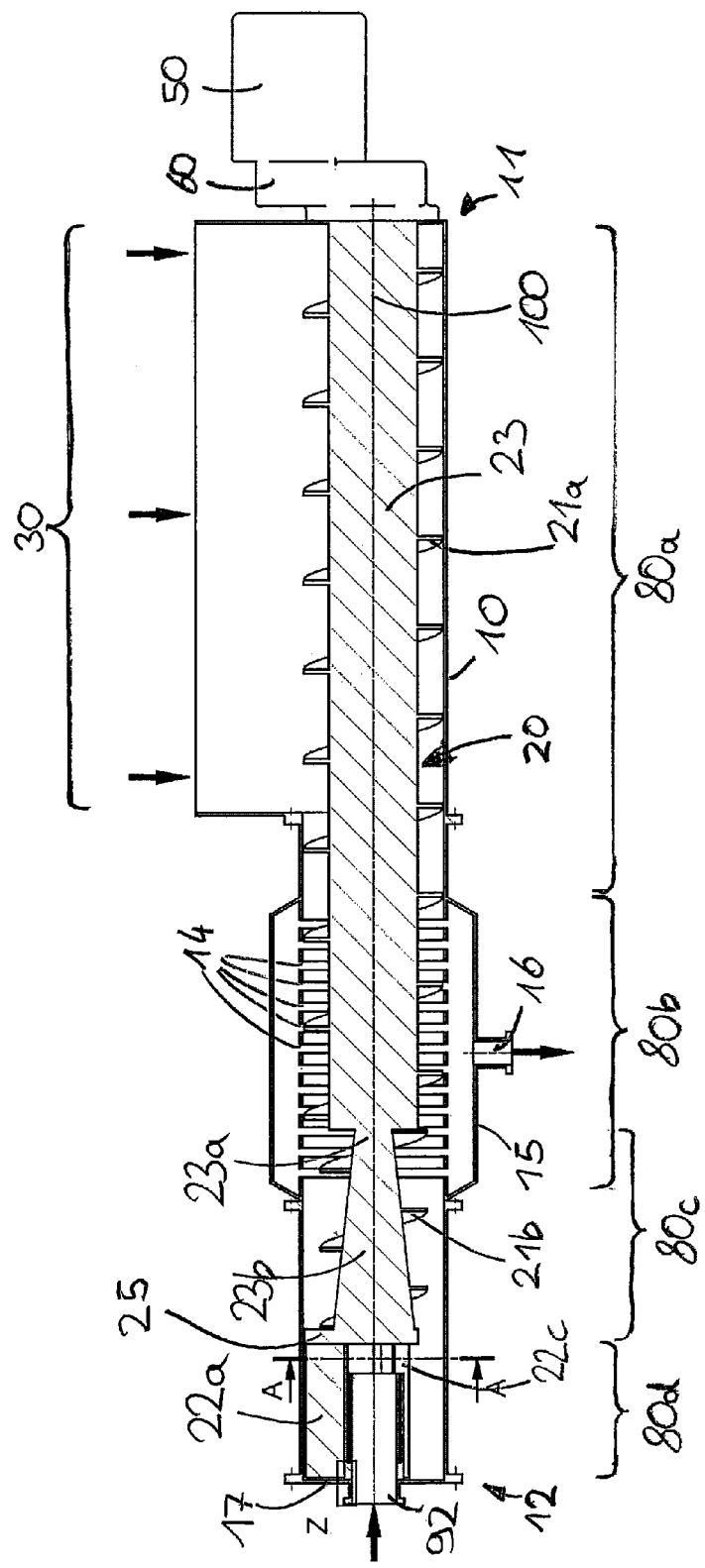
FIG. 1 shows a vertical longitudinal cross-sectional side view of a screw conveyor according to the invention.
Figure 2:
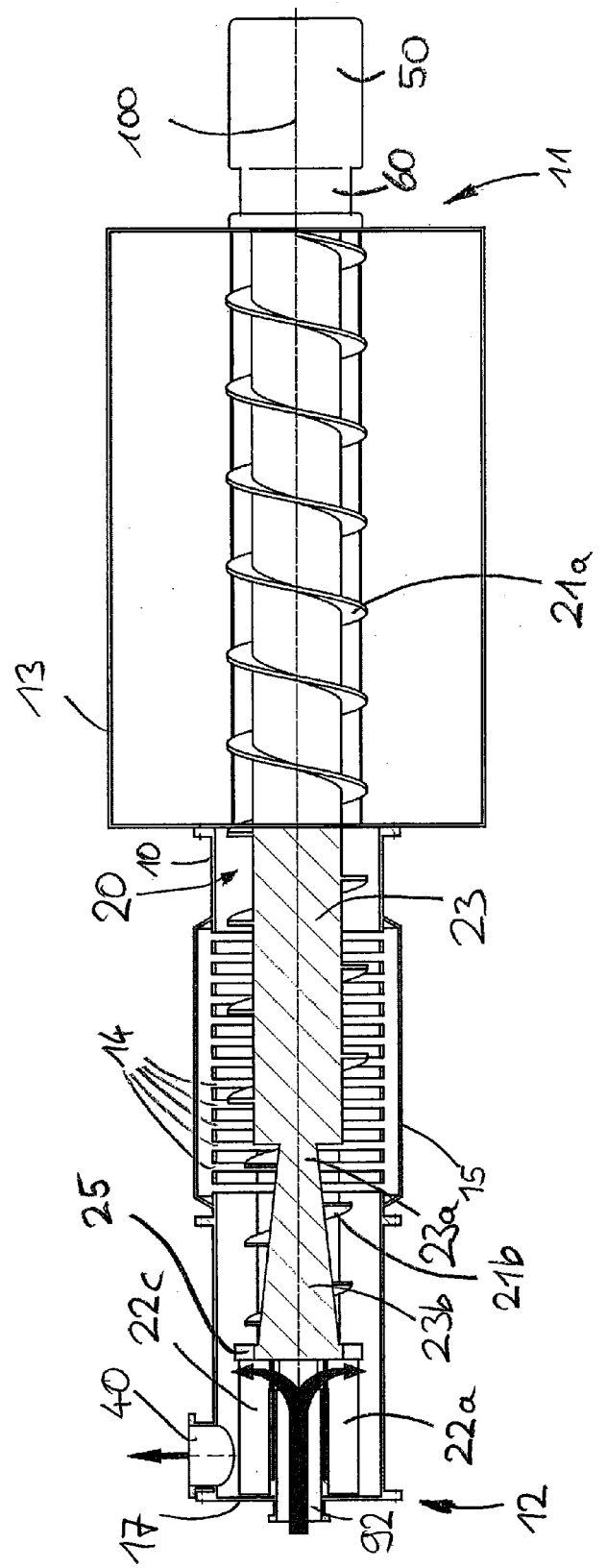
FIG. 2 shows a horizontal partial longitudinal cross-sectional plan view of the screw conveyor according to FIG. 1.
Figure 3:
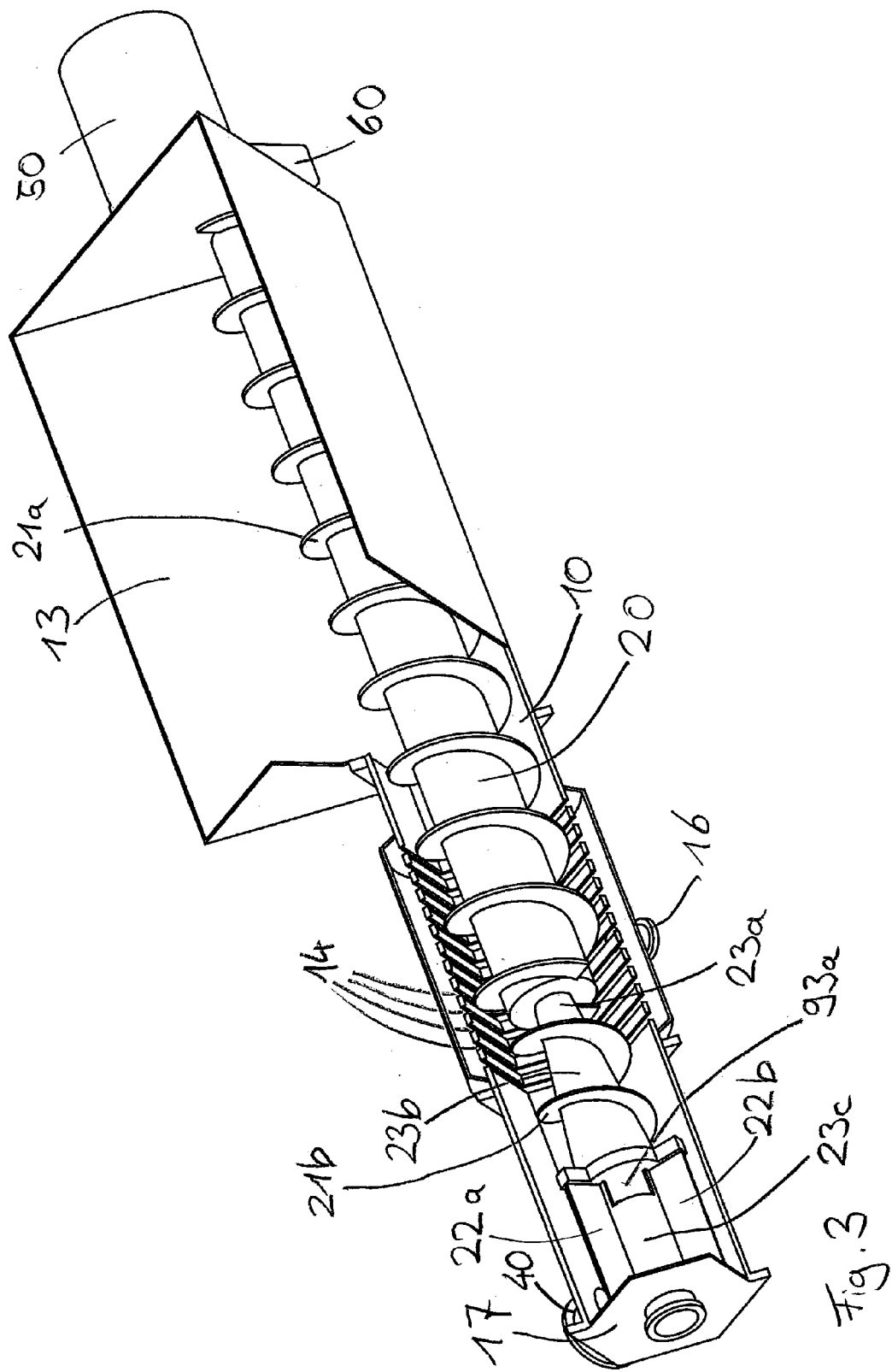
FIG. 3 shows a partly cutaway perspective view of the screw conveyor according to FIGS. 1 and 2.

In FIGS. 1, 2 and 3, a screw conveyor 1 is shown that basically comprises a screw pipe 10 in which a conveying screw 20 is mounted rotatably about a longitudinal axis 100. The conveying screw comprises a conveying screw core 23 and flights 21a, 21b and 22a-c.

An inlet opening 30 extends from a first end 11 of screw pipe 10 in the axial direction towards a second end 12 of screw pipe 10 across about half of the total length of screw pipe 10. Inlet opening 30 is in the form of a screw trough 13 and allows organic solids to be fed radially into screw pipe 10.

An outlet opening 40 in the form of a flange is disposed in the region of the second end 12, said outlet opening 40 likewise extending radially and having a direction of discharge that is rotated by 90 degrees about the longitudinal axis 100 relative to the direction in which the organic solids are fed into inlet opening 30.

At the first end 11 of screw pipe 10, an electrical drive motor 50 is flanged to the casing pipe via an intermediate gear 60. Drive motor 50 rotates conveying screw 20 about the longitudinal axis 100 via intermediate gear 60.

Conveying screw 20 has a first screw conveyor section 80a which extends across the entire region of the inlet opening and which also includes a region adjacent thereto, in which conveying screw 20 is surrounded by a closed pipe section of the conveyor pipe. In this first screw conveyor section 80a, conveying screw 20 has a conveying screw core 23 of constant diameter and flighting 21a of constant outer diameter disposed thereon. Flights 21a are embodied as a single-start thread which winds around the conveying screw core in the longitudinal direction.

It should be understood that the pitch may be constant for flight 21a across the entire length of this first screw conveyor section 80a. However, in a section of the first screw conveyor 80a adjacent to motor 50, a smaller flighting pitch may be provided than in a section of the screw conveyor 80a lying further ahead in the conveying direction, so that screw trough 13 is emptied in an axially uniform manner.

The first screw conveyor section 80a is followed in the conveying direction by a second screw conveyor section 80b. In this second section 80b, the screw pipe is perforated by a plurality of openings 14 and is surrounding by a housing 15. In this separation section 80b, fluid escapes from the screw pipe through openings 14, thus resulting in dewatering of the organic solids. The fluid which escapes is collected in housing 15 and is discharged through a pipe connection 16 which points downwards in the direction of gravity.

A third screw conveyor 80c follows this second screw conveyor section 80b in the conveying direction and its functions may partly overlap those of the latter. Whereas the conveying screw in the second section 80b is embodied in the same way as in the first section 80a, the diameter of conveying screw 23 is reduced in steps in the third section 80c to a significantly reduced core diameter in a region 23a. This reduction occurs in the inlet region of the third section 80c and results in an increase in the passage cross-section. Starting from this reduction, the diameter of the conveying screw core is then increased again to the original diameter of the conveying screw core, which is also constant in the first and second sections 80a, b. This expansion is effected by a conical design in a region 23b extending over practically the entire length of the third section 80c. This increase results in the passage cross-section being reduced.

In this third section 80c, which functions as a plug section, flights 21b may be designed with a pitch that decreases in the conveying direction, in order to reinforce the compacting effect. Flights 21b may have a smaller outer diameter in section 80c than in section 80b and may be designed with a constant outer diameter. Due to the increasing core diameter in plug section 80c, this results in the flights having a decreasing radial depth in the conveying direction. The screw pipe is provided in the initial region of plug section 80c with small openings, so plug section 80c and separation section 80b functionally overlap in part. In a middle and end region of plug section 80c that then follows in the conveying direction, the screw pipe is again closed as in section 80a.

Inside plug section 80c, at its rear, downstream end (on the left in FIGS. 1 and 2), a compacted plug of organic solids is formed that provides a reliable seal against any undesired escape of solids, liquids or gases during operation or stoppages of the screw conveyor.

Figure 5A:
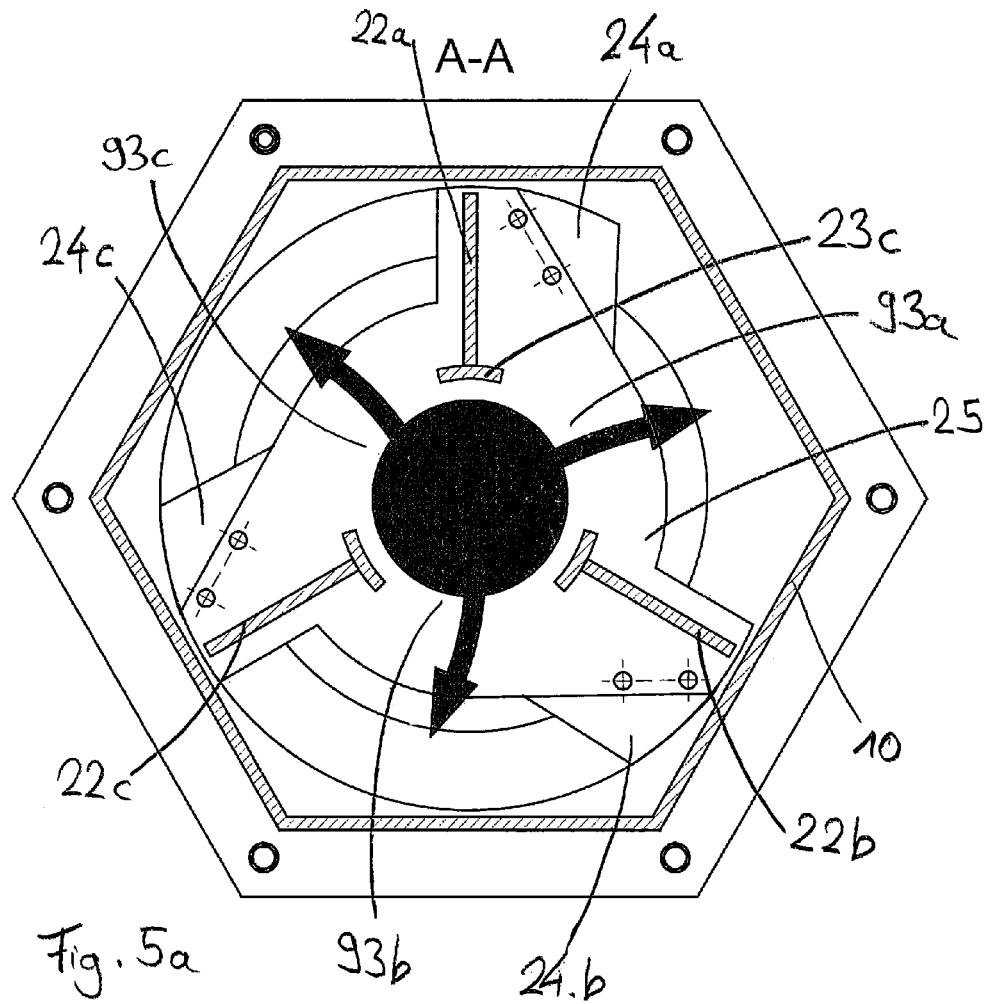
FIG. 5a shows a transverse cross-sectional view along line A-A in FIG. 1, without mounted flights.
Figure 5B:
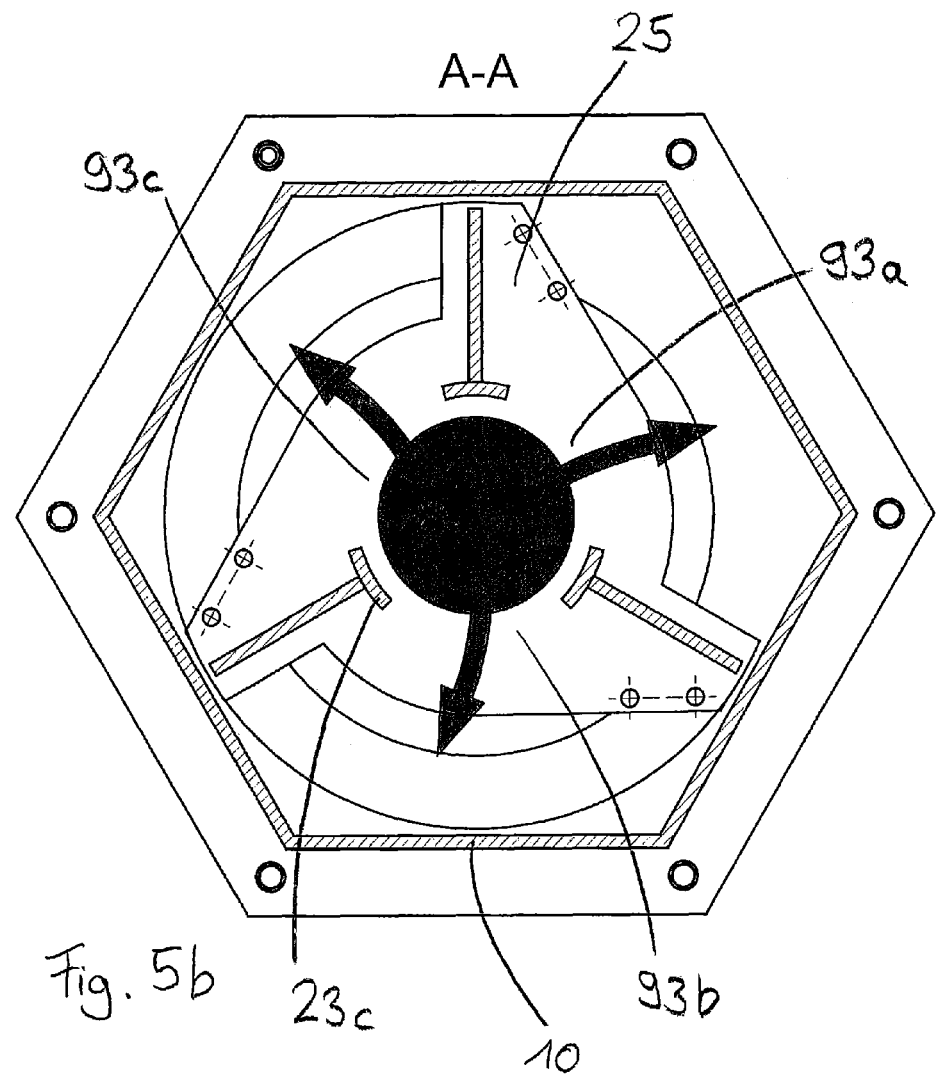
FIG. 5b shows a transverse cross-sectional view along line A-A in FIG. 1, with the flights dismantled.

Plug section 80c is then followed in the conveying direction by a fourth screw conveyor section 80d which functions as an ejection section. As can be seen from FIGS. 5a, b in particular, three flights 22a-c extending in the axial direction and having a greater pitch than flights 21a, b are mounted in ejection section 80d. These three flights 22a-c are attached to the conveying screw core embodied as a hollow shaft 23c in section 80d.

Between plug section 80c and ejection section 80d, there is also a flange 25 which is fixed torque-resistantly to conveying screw 20. Sets of two bores are formed and distributed at intervals of 120° on the flange, said bores being used to selectively mount and replace three flights 24a-c, for example to adapt the passage cross-section in FIGS. 5a, b to the consistency of the conveyed solids by means of the three flight 22a-c.

Flight 22a-c and 24a-c cause the conveyed organic solids to be ejected efficiently and radially outwards through opening 40. Flights 24a-c may additionally cause the conveyed solids to be comminuted and can therefore operate as rotating cutting blades.

Figure 4:
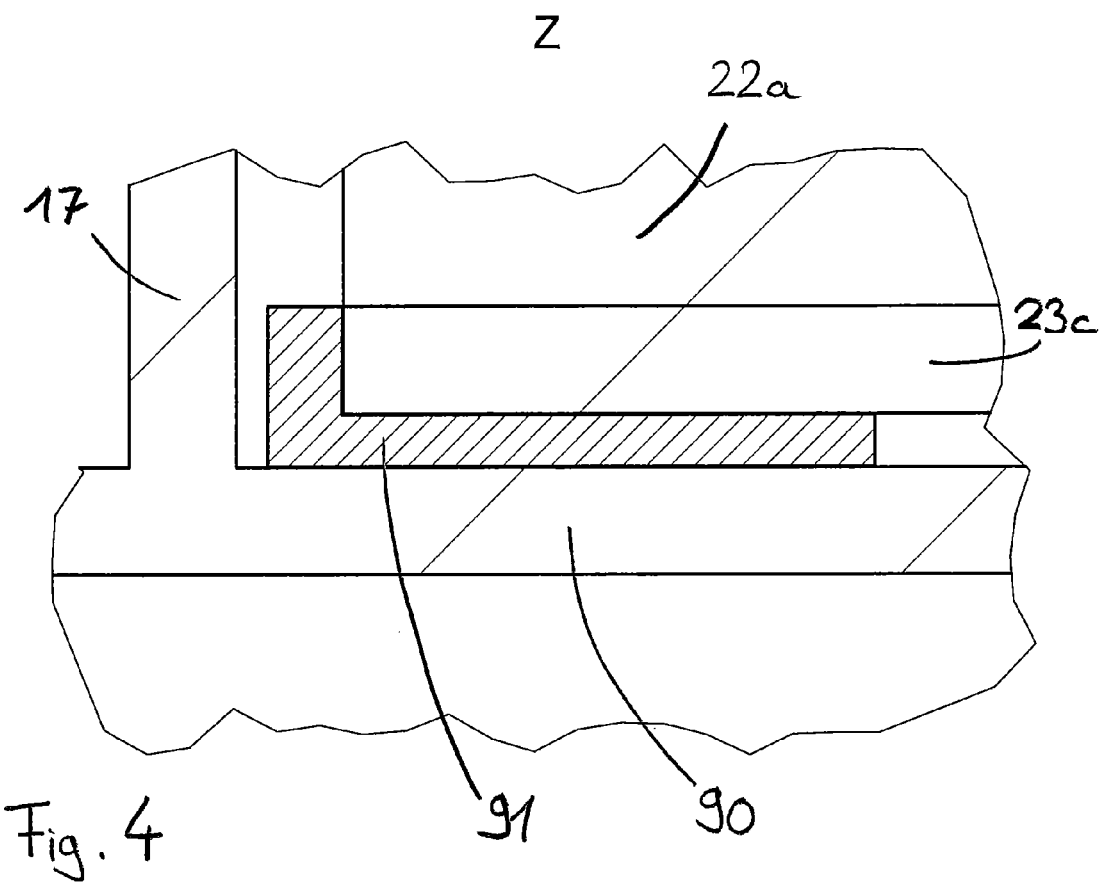
FIG. 4 shows a detailed view of the detail marked Z in FIG. 1.

In the region of ejection section 80d, conveying screw 20 is embodied as a hollow shaft 23c and encloses a pipe connection 90 which is mounted torque-resistantly in an end wall 17 at end 12 of the screw pipe. As can be seen from FIG. 4, in particular, conveying screw 20 is rotatably mounted by means of a sliding bearing bushing 91 on pipe connection 90 in the region of the second end 12.

Pipe connection 90 has an inlet opening 92 through which a flushing fluid can be flushed in in the axial direction. As indicated by the branching arrow in FIG. 2, this flushing fluid is conducted through pipe connection 90 and discharged in the radial direction into the passage cross-section in the region of ejection section 80d. As can be seen from FIG. 3, three radial outlet openings 93a-c are provided for this purpose on the conveying screw embodied as a hollow shaft, and cause fluid to be discharged between flights 22a-c. The previously compacted solid material is diluted, and its viscosity is reduced, by the flushing fluid introduced in this manner, with the result that the material is efficiently ejected through outlet opening 40.

It can also be seen from FIG. 3 that screw pipe 10 has a hexagonal cross-section. Flights 21a, 22a-c and 24a-c have an outer diameter that is congruent, with a slight amount of play, with a circle drawn inside the hexagon thus defined. The passage cross-section through the screw conveyor is thus defined by an outer hexagonal boundary, by the screw pipe, and by an inner, circular boundary by the core of the conveying screw, and is also slightly reduced by the cross-section of flights 21a, b, 24a-c and 22a-c.

That which is claimed:

1. A screw conveyor for introducing organic matter into a biogas digester that is under internal gas pressure, said screw conveyor comprising:
   a screw pipe extending in a longitudinal direction and having an inlet opening for organic matter in the region of a first screw pipe end, and an outlet opening for the organic matter in the region of a second screw pipe end, and an inner wall,
   a conveying screw (i) extending in the longitudinal direction, (ii) arranged inside the screw pipe, and (iii) which is made to rotate by a screw conveyor drive, for conveying the organic matter in a conveying direction, and spaced from the inner wall so as to form a passage cross-section, and
   a digester connector for connecting the outlet opening directly to the biogas digester,
   wherein the screw pipe comprises a plug section in a region between the inlet opening and the outlet opening for compacting the organic matter in order to reduce any passage of gas through the screw conveyor, and
   wherein the plug section has an expansion region in which the passage cross-section increases in the conveying direction, and a contraction region disposed downstream from the expansion region, in which the passage cross-section decreases in the conveying direction.

2. The screw conveyor according to claim 1, wherein the spacing between the conveying screw and the inner wall forms a first pre-plug passage cross-section in a region before the expansion region in the conveying direction, the first pre-plug passage cross-section being less than the passage cross-section in the expansion region.

3. The screw conveyor according to claim 1, wherein the passage cross-section in the plug section increases in steps in the conveying direction in the expansion region.

4. The screw conveyor according to claim 1, wherein the passage cross-section changes before the plug section in the conveying direction, starting from a first passage cross-section having a cross-sectional geometry characterised by a first ball passage, to a second passage cross-section having a cross-sectional geometry characterised by a second ball passage that is larger than the first ball passage, and changes further to a third passage cross-section having a cross-sectional geometry characterised by a third ball passage which is smaller than the second ball passage, wherein the first and the third ball passages are congruent.

5. The screw conveyor according to claim 1 in which the conveying screw comprises a screw core and at least one flight which is disposed in the region of the second screw pipe end and which is detachably fixed to the screw core.

6. The screw conveyor according to claim 5, wherein the at least one flight comprises (a) a first flight which is mounted on the screw conveyor and (b) a second flight which is mounted to the first flight and which has a cross-section that fills out a larger cross-sectional area, relative to the first flight, of the passage cross-section.

7. The screw conveyor according to claim 1, wherein the inner wall of the screw pipe encloses a non-circular inner cross-sectional area.

8. The screw conveyor according to claim 7, wherein the inner wall of the screw pipe encloses a polygonal inner cross-sectional area.

9. The screw conveyor according to claim 1, wherein the inlet opening is designed-as-a radial opening in the screw pipe and extends across an inlet opening section in the longitudinal direction of the screw pipe, and that in the region of the inlet opening section the conveying screw has a fighting pitch comprising a first flighting pitch and a second flighting pitch differing from the first flighting pitch.

10. The screw conveyor according to claim 9, wherein the flighting pitch continuously changes in the region of the inlet opening section.

11. The screw conveyor according to claim 9, wherein the fighting pitch is shorter in the region of the inlet opening section facing the first screw pipe end than in the region of the inlet opening section facing the second screw pipe end.

12. The screw conveyor according to claim 1, wherein the outlet opening is connected by the digester connector directly to a solid matter feed opening of the biogas digester or to a pipeline that is under internal digester pressure and which leads to the solid matter feed opening of the biogas digester.

* * * * *

UNITED STATES PATENT AND TRADEMARK OFFICE
CERTIFICATE OF CORRECTION

PATENT NO. : 9,650,598 B2
APPLICATION NO. : 14/356707
DATED : May 16, 2017
INVENTOR(S) : Hugo Vogelsang Page 1 of 1

It is certified that error appears in the above-identified patent and that said Letters Patent is hereby corrected as shown below:

On the Title Page

In Item (30), under Foreign Application Priority Data, delete "20 2011 107 750 U" and insert -- 20 2011 107 750.4 -- therefor.

In the Claims

In Column 10, Line 20 delete "and".

In Column 11, Line 10 delete "designed as".

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*